United States Patent
Miyazaki et al.

(10) Patent No.: US 6,320,377 B1
(45) Date of Patent: Nov. 20, 2001

(54) MR IMAGING WITH PRE-SEQUENCE INCLUDING PLURAL SATURATION PULSES

(75) Inventors: Mitsue Miyazaki; Satoshi Sugiura, both of Otawara (JP)

(73) Assignee: Kabushiki Kaisha Toshiba, Kanagawa-ken (JP)

( * ) Notice: Subject to any disclaimer, the term of this patent is extended or adjusted under 35 U.S.C. 154(b) by 0 days.

(21) Appl. No.: 09/048,290

(22) Filed: Mar. 26, 1998

(30) Foreign Application Priority Data

Mar. 28, 1997 (JP) .................................................. 9-078559
Mar. 19, 1998 (JP) ................................................ 10-070941

(51) Int. Cl.[7] .............................. G01V 3/00; A61B 5/05
(52) U.S. Cl. ........................... 324/306; 324/307; 324/309
(58) Field of Search ................................ 324/128.6, 53.2, 324/300–322; 600/408, 410, 411, 413

(56) References Cited

U.S. PATENT DOCUMENTS

| | | | |
|---|---|---|---|
| 4,715,383 | * 12/1987 | Ehman et al. | 324/309 |
| 5,034,694 | * 7/1991 | Sattin et al. | 324/309 |
| 5,447,155 | * 9/1995 | NessAvier et al. | 128/653.2 |
| 5,517,117 | * 5/1996 | Mueller et al. | 324/306 |
| 5,528,144 | * 6/1996 | Gullapalli et al. | 324/306 |
| 5,633,586 | * 5/1997 | Finn | 324/309 |
| 5,677,628 | * 10/1997 | Watanabe et al. | 324/309 |
| 6,043,655 | * 3/2000 | Makita et al. | 324/309 |

OTHER PUBLICATIONS

Miyazaki et al, "A Polarity Altered Spectral and Spatial Selective Acquisition Technique", SMR Abstract #657, 1995.

Martin R. Prince, "Gadolinium–enhanced MR Aortography," Radiology 1994, 191; 155–164.

J. H. Kim and Z. H. Cho, "3–D MR Angiography with Scanning 2–D images–simultaneous Data Acquisition of Arteries and Veins (SAAV)," Magnetic Resonance in Medicine 14, 554–561 (1990).

* cited by examiner

Primary Examiner—Hezron Williams
Assistant Examiner—Tiffany H. Fetzner
(74) Attorney, Agent, or Firm—Nixon & Vanderhye P.C.

(57) ABSTRACT

An artery vein visually separated MRA image and/or a higher blood/parenchyma contrast MRA image are provided by a magnetic resonance imaging system. The system comprises, in addition to a magnet generating a static magnetic field, a gradient generation unit generating magnetic gradients superimposed on the static magnetic field, a transmission/reception unit transmitting to a subject spin-exciting RF signal and receiving an MR signal emanated from the subject, a reconstruction unit reconstructing the image based on the MR, and a sequencer for performing a scan sequence of pulses through control of the gradient generation unit and the transmission/reception unit. The scan sequence of pulses is formed for producing the functions of: applying not only a plurality of saturation pulses in time series to a pre-saturated slice positionally different from the imaging slice but also a slice gradient pulse for selecting the pre-saturated slice concurrently with the plurality of saturation pulses, and performing a data acquisition sequence applying to the imaging slice a pulse train for acquiring an MR signal from the imaging slice after application of the plurality of saturation pulses and the slice gradient pulse.

30 Claims, 13 Drawing Sheets

MR IMAGING WITH PRE-SEQUENCE INCLUDING PLURAL SATURATION PULSES

BACKGROUND OF THE INVENTION

1. Field of the Invention

The present invention relates to a magnetic resonance imaging (MRI) technique referred to as magnetic resonance (MR) angiography, which acquires images of blood vessels of subjects, based on a magnetic resonance phenomenon occurring in the subjects. More particularly, the present invention is concerned with a magnetic resonance imaging system and magnetic resonance imaging method based on an improved MR angiography technique using a plurality of saturation pulses applied with slice-selective gradient pulses, the saturation pulses being used for separation between arteries and veins, suppression of body motion artifacts, and the like.

2. Description of the Related Art

Magnetic resonance imaging is a technique for magnetically exciting nuclear spins existing in a subject positioned in a static magnetic field by applying a radio-frequency signal with the Larmor frequency, and reconstructing an image using an MR signal induced with the excitation or producing a spectrum of the MR signal.

In the field of MRI, MR angiography techniques for imaging flows of blood within a subject or measuring the flow speed thereof have already been in practical use in medical examination. One of the MR angiography techniques uses a saturation pulse, applied with a slice-selective gradient, causing proton spins of flows of blood to be pre-excited and saturated at the time of acquisition of MR signals.

In the conventional saturation pulse based technique, a signal saturation pulse is applied to a slice positioned upstream or downstream across flows of blood passing through an imaging slice. For example, in the case of imaging the inferior limb, since the directions of flows of blood are opposite to each other between the arteries and veins, a single saturation pulse is applied to a preliminary slice set at an upstream or downstream side to an objective imaging slice, and then echo signals are acquired from the imaging slice using, for example, an FE method. Since the spins (dipoles of magnetization) of the arteries or veins inflowing the imaging slice have already been excited and saturated, they are no longer excited by the succeeding MR data acquisition sequence, thereby reducing the strength of MR signals induced from the blood flow. By contrast, the saturation pulse has not been applied to arteries or arteries inflowing the imaging slice from the opposite side, MR signals of higher strength are acquired from those blood vessels. It may therefore be expected that the arteries and veins be separated from each other on a reconstructed MR image.

However, speeds of blood flows in an imaged region are sometimes very fast or slow (particularly, in the inferior limb, they are slow). In such cases, owing to the fact that a flow-void phenomenon occurs or the inflow of saturated spins becomes extremely slow, the effectiveness of applying the saturation pulse is not enough, thereby providing no images where arteries and veins are distinctly visual-separated from each other.

Additionally, for the limbs, in general, the speeds of pulsated blood flows become remarkably slow depending on distances along peripheral vessels. To be specific, when the sequence incorporating the conventional saturation pulse is used, the blood flows of the inferior limb themselves can hardly be imaged because of the time of flight effect is less. Yet, for example, for knee diseases, to meet a clinical demand that artery-vein clearly separated images are desired is beyond the conventional imaging technique.

Another MR angiography technique different from the sequence using the saturation pulse is under research, which is trying the visual separation between arteries and veins. According to this research, MR contrast medium is injected into a patient and arteries and veins are visually separated based on differences between temporal changes in contrast for arteries and veins.

For MR angiography using MR contrast medium, however, invasiveness due to the injection of MR contrast medium is very large, requiring patients to endure it.

Further in the case of using MR contrast medium, since the actual contrast effect for inferior limb is low, differences in contrast peak times between arteries and veins are small. Thus, for the present, no clear separation images are provided.

Therefore, any conventional MR angiography technique is not suitable for such regions as the limbs where the speeds of blood flows are extremely low. It is almost impossible to provide high-quality artery-vein separated images with non-invasive treatment.

SUMMARY OF THE INVENTION

The present invention attempts to break through the foregoing current situation of known arts. Specifically, an object of the present invention is to provide, with sustaining non-invasiveness which is inherent to MR imaging, MRA images of higher contrast between blood and parenchyma even when the speeds of blood flows are extremely large or small.

Another object of the present invention is to provide, with higher contrast between blood flows and parenchyma, MRA images where arteries and veins are visually separated in a steady manner.

Still another object of the present invention is to create a situation in which a variety of types of scan sequences can be executed with higher contrast between blood flows and parenchyma as well as a steady visual separation of arteries and veins.

For accomplishing the above objects, one aspect of the present invention relates to an magnetic resonance system obtaining an image representing a blood vessel in an objective imaging slice of a subject, comprising: first means for performing a pre-sequence including a plurality of saturation pulses time-sequentially applied to a pre-saturated slice positionally different from the imaging slice; and second means for performing a data acquisition sequence for acquiring an MR signal from the imaging slice after the performance of the pre-sequence.

It is preferred that the pre-sequence includes a slice gradient pulse for being applied in parallel with the plurality of saturation pulses and used for a spatial position of the pre-saturated slice. As one example, the slice gradient pulse consists of a plurality of slice gradient pulses each applied in parallel with each of the plurality of slice gradient pulses. Still another example is that the plurality of saturation pulses are determined to have a time interval of zero between two adjacent pulses of the saturation pulses.

It is also preferred that the slice gradient pulse consists of a single slice gradient pulse continuously applied in parallel with all the plurality of saturation pulses.

It is still preferred that pre-sequence includes a plurality of gradient spoilers each applied to the subject after each of the plurality of saturation pulses.

Further preferred is that the pre-sequence includes a gradient spoiler applied to the subject after application of a last temporal saturation pulse in a train consisting of the plurality of saturation pulses. By way of example, the gradient spoiler includes at least a gradient spoiler applied in the slice direction. Another example is that the gradient spoiler includes three gradient spoiler pulses applied in three directions, respectively, consisting of the slice direction and a phase-encoding and read-out directions perpendicular to the slice direction.

Preferably, each of the plurality of saturation pulses is given a flip angle of spins less than 100 degrees.

Still preferably, at least one of the plurality of saturation pulses is given a flip angle of spins determined differently from its remaining saturation pulses. For example, each of the plurality of saturation pulses is given a flip angle of spins different from one another. It may be employed that the flip angle of each of the plurality of saturation pulses lowers gradually as going forward in an application time.

Preferably the slice gradient is formed such that both the pre-saturated slice and the imaging slice become parallel or thereabout to each other.

Still preferred is that the data acquisition sequence is a pulse train of a fast SE sequence family constituting part of a fast FLAIR sequence in which an inversion pulse is applied and the pulse train is applied after an interval of an inversion time from the inversion pulse. In this case, for example, the first performing means is constructed to perform the pre-sequence during the interval of the inversion time. For example, the first performing means is constructed to repeat a plurality of times the pre-sequence based on a multislice technique. The second performing means is constructed to repeat the data acquisition sequence, based on the multislice technique a, plurality of time which is the same as the number of pre-sequenced repetitions. One example is that the first and second performing means are constructed to repeat in time series the pre-sequence and data acquisition sequence in an interleaved mode for each of a plurality of slices multi-sliced on the multislice technique, each slice corresponding to the imaging slice.

Another aspect of the present invention is provided by a magnetic resonance imaging system obtaining an image representing a blood vessel in an objective imaging slice of a subject, comprising: a magnet for generating a static magnetic field into a space in which the subject is placed; a gradient generation unit for generating via gradient coils slice, phase-encoding, and read-out magnetic gradients superimposed on the static magnetic field; a transmission/reception unit for via an RF coil transmitting to the subject a spin-exciting RF signal and receiving an MR signal emanated from the subject; a reconstruction unit for reconstructing the image based on the MR signal received by the reception unit; and a sequencer for performing a scan sequence of pulses through control of the gradient generation unit and the transmission/reception unit, the scan sequence of pulses being formed for producing the functions of: applying not only a plurality of saturation pulses in time series to a pre-saturated slice positionally different from the imaging slice but also a slice gradient pulse for selecting the pre-saturated slice concurrently with the plurality of saturation pulses, and performing a data acquisition sequence applying to the imaging slice a pulse train for acquiring an MR signal from the imaging slice after application of the plurality of saturation pulses and the slice gradient pulse.

Further, as another aspect of the present invention, there is a method of imaging a magnetic resonance image representing a blood vessel in an objective imaging slice of a subject, comprising the steps of: applying in time series a plurality of saturation pulses to a pre-saturated slice selected positionally different from the imaging slice; applying to the object a gradient spoiler for dephasing spins thereof; acquiring an MR signal from the imaging slice; and producing the magnetic resonance image using the acquired MR signal.

Accordingly, applying a plurality of saturation pulses permits a steady suppression of MR signal acquired from arteries or veins even if the speeds of blood are extremely fast or slow, thereby providing an MRA image where the arteries and veins are visually and distinctly separated from each other. Further, the application of a plurality of saturation pulses to the same pre-saturated slice causes not only the stationary parenchyma of an imaging slice to have a larger magnetization transfer effect but also flowing blood to have a smaller MT effect. For blood passing the pre-saturated slice, a plurality of saturation pulses operates as if a single saturation pulse of a divided small flip angle was applied. Hence it is possible to provide MRA images of a higher contrast of blood to parenchyma and a higher visibility. Providing such high-quality images without using MR contrast medium still sustains non-invasiveness, relieving patients of their physical and/or mental burden.

The features of the invention will be clearly understood from the description of various preferred embodiments, which are described with accompanying drawings below.

DESCRIPTION OF THE PREFERRED EMBODIMENTS

Figure 1:
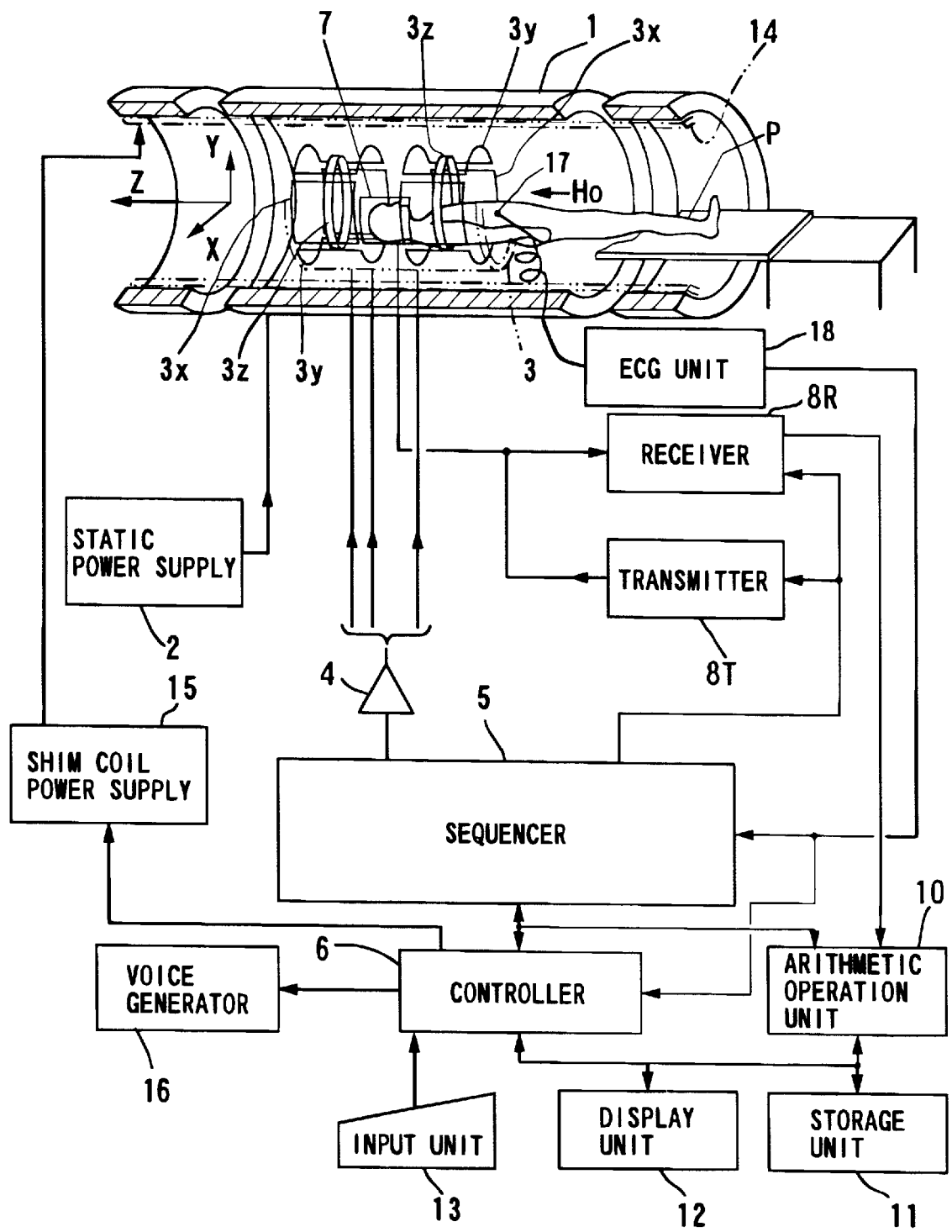
FIG. 1 is a block diagram showing an example of an MRI system in accordance with the embodiments of the present invention.

FIG. 1 shows the outline configuration of a magnetic resonance imaging (MRI) system in accordance with the embodiments of the present invention.

The MRI system comprises a patient couch on which a patient P lies down, static magnetic field generating components for generating a static magnetic field, magnetic field gradient generating components for appending positional information to a static magnetic field, transmitting receiving components for transmitting and receiving a radio-frequency signal, control and arithmetic operation components responsible for control of the whole system and for image reconstruction, and an electrocardiographing component for acquiring an ECG signal of a patient.

The static magnetic field generating components includes a magnet 1 that is of, for example, a superconducting type, and a static power supply 2 for supplying a current to the magnet 1, and generates a static magnetic field $H_0$ in an axial direction (Z-axis direction) in a cylindrical bore (diagnostic space) into which the patient P is inserted. The magnet unit includes shim coils 14. A current used to homogenize a static magnetic field is supplied from a shim coil power supply 15 to the shim coils 14 under the control of a controller to be described later. The couch top of the patient couch on which the patient P lies down can be inserted into the bore of the magnet 1 so that the couch top can be withdrawn.

The magnetic field gradient generating components includes a gradient coil unit 3 incorporated in the magnet 1. The gradient coil unit 3 includes three pairs (kinds) of x, y, and z coils 3x to 3z used to generate magnetic field gradients changing in strength in X-axis, Y-axis, and Z-axis directions that are mutually orthogonal in the physical coordinate system of the MRI system. The magnetic field gradient generator further includes a gradient power supply 4 for supplying a current to the x, y, and z coils 3x to 3z. The gradient power supply 4 supplies a pulsating current used to generate a magnetic field gradient to the x, y, and z coils 3x to 3z under the control of a sequencer 5 that will be described later.

The pulsating current supplied from the gradient power supply 4 to the x-, y-, and z-coils 3x to 3z is controlled, whereby magnetic field gradients changing in the three axial directions, that is, the X-, Y-, and Z-directions are synthesized. Thus, directions in which a slice gradient pulse $G_S$, a phase-encoding magnetic field gradient $G_E$, and a read-out (frequency-encoding) magnetic field gradient $G_R$ are applied can be specified and changed arbitrarily. The magnetic field gradients to be applied in a slice direction, a phase-encoding direction that is a direction in which the distribution of spins is phase-encoded, and a read-out direction that is a direction in which an MR signal is read are superposed on the static magnetic field $H_0$.

The transmitting/receiving components includes a radio-frequency coil 7 located in the vicinity of the patient P in the scanning space inside the magnet 1, and a transmitter 8T and receiver 8R connected to the coil 7. The transmitter 8T and receiver 8R supply radio-frequency pulses with the Larmor frequency, which are used to excite magnetic resonance (MR), under the control of the sequencer 5 to be described later, after an echo time TE receive an MR signal (radio-frequency signal) via the radio-frequency coil 7, carries out various kinds of signal processing, and then produces a corresponding digital signal.

Furthermore, the control and arithmetic operation components includes the sequencer 5, a controller 6, an arithmetic operation unit 10, a storage unit 11, a display unit 12, an input unit 13, and a voice generator 16. Among them, the controller 6 includes a computer. The controller 6 has the function of following a procedure that is a software program stored in the computer so as to command the sequencer 5 to provide pulse-sequence information, matching in timing the operations of the control blocks including the sequencer 5 in the whole system, and managing the control blocks on a centralized basis.

In the MRI system, prior to acquiring MR data of an objective imaging slice, a pre-saturated slice which includes flows of blood flowing into the imaging slice and differs in spatial position from the imaging slice is subject to a pre-sequence. In the pre-sequence, the pre-saturated slice is slice-selectively pre-saturated by a plurality of saturation pulses consecutively applied. The pre-saturated slice is, for example, a parallel slice adjacent to the imaging slice with or without a gap, or an oblique slice to the imaging slice. This pre-saturation is followed by a gradient spoiler pulse for dephasing spins.

Figure 2:
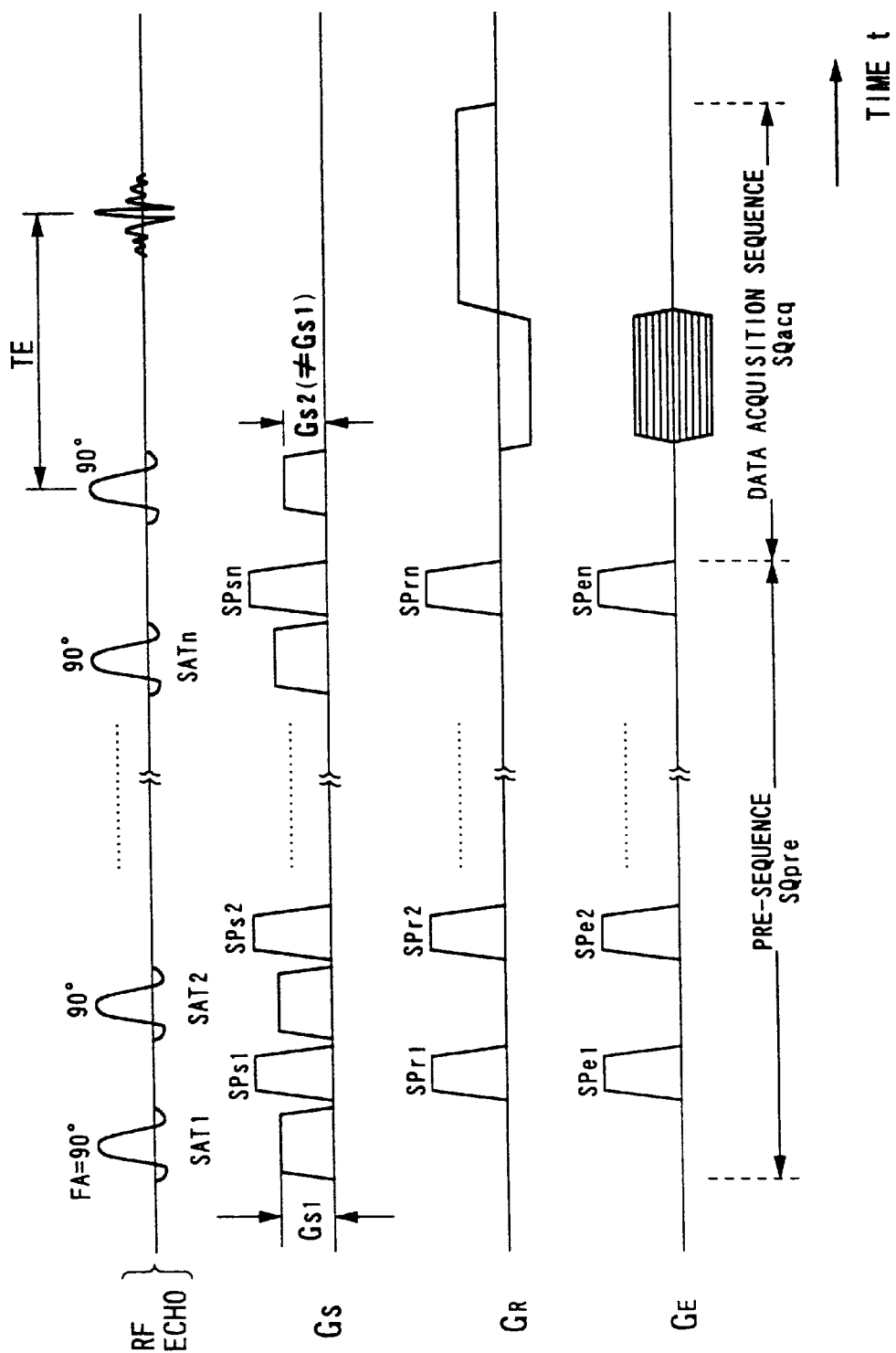
FIG. 2 is an example of a scan sequence to be executed in a first embodiment of the present invention.

To realize this, the controller 6 and sequencer 5 are cooperatively operated to execute a scan based on a scan sequence for MR angiography shown in FIG. 2. The scan sequence is comprised of a pre-sequence $SQ_{pre}$ for first pre-saturating blood spins and a succeeding data acquisition sequence $SQ_{acq}$. The scan will be computer-executed in response to a predetermined main program processed by the controller 6. MR signals acquired by executing the scan will be formed into MRA images through reconstruction by the arithmetic operation unit 10.

The sequencer 5 has a CPU and memory, stores scan-sequence information sent from the controller 6, and controls a series of operations to be performed by the gradient power supply 4, transmitter 8R, and receiver 8T according to the stored information. What is referred to scan-sequence information is all information required for operating the gradient power supply 4, transmitter 8R, and receiver 8T according to a scan sequence. For example, scan-sequence information includes information concerning the strength of a pulsating current to be applied to the x, y, and z coils 3x to 3z, and the application time and timing thereof. Still, the sequencer 5 is constructed such that it executes the above-described timing control in synchronism with a gating pulse derived from a latter-described ECG signal of a subject.

As for the data acquisition sequence forming part of an entire scan sequence, for example, a pulse sequence used for two-dimensional (2D) or three-dimensional (3D) scanning will do as long as the Fourier transform can be applied for image reconstruction. Such sequence may be of a wide range of pulse trains such as spin echo (SE), field gradient echo (FE), fast SE (FSE), fast advanced SE (FASE) using the fast SE based on a half-Fourier method, FLAIR (Fluid Attenuated Inversion Recovery), fast FLAIR, echo planar imaging (EPI), Hybrid EPI, or the like.

The arithmetic operation unit 10 inputs digital raw data corresponding to an MR signal sent from the receiver 8R, maps the raw data in the Fourier space (or the k-space or frequency space) formed in an incorporated memory, and performs a two-dimensional Fourier transform on the raw data so as to reconstruct an image in the real space. Additionally the arithmetic operation unit 10 carries maximum intensity projection (MIP) processing by which maximum pixel values are selected pixel by pixel from reconstructed image data of a plurality of frames constituting a three-dimensional image data of a volume region scanned, each frame being scanned on the basis of the invention technique.

The storage unit 11 can preserve not only raw data and reconstructed image data but also image data having undergone arithmetic operation. The display unit 12 displays an image, and can be used to input desired information entered at the input unit 13 by an operator; such as, desired scan conditions, a desired scan sequence, and a technique of image processing to the controller 6.

The voice generator 16 utters, for example, a voice message informing the start and end of breath hold in response to a command sent from the controller 6.

The electrocardiographing component is made up of an ECG (electrocardiograph) sensor 17 attached to a patient P and outputting an electric ECG signal of the patient and an ECG sensor 18 outputting a gate pulse as an ECG gating signal to the controller 6 and sequencer 5, the gate pulse having a minute pulse width synchronous with the peak values of R-waves of the ECG signal. The gate pulses are utilized by sequencer 5 as the ECG gating signal to control each start timing of scanning. The control enables to be set appropriate ECG gated timing, making it possible to acquire MR unprocessed (raw) data based on the ECG gated scan.

The operation of the MRI system according to the first embodiment will now be described.

The controller 6 performs a scan sequence of pulses shown in FIG. 2 in the course of performing a specified main program (not shown). The pulses included in the scan sequence are applied via the x, y, and z-coil 3x to 3z and RF coil 7 under the control of the sequencer 5 managed by the controller 6.

As shown in FIG. 2, the scan sequence consists of a pre-sequence $SQ_{pre}$ serving as a saturation sequence including saturation pulses exciting and saturating proton spins and a data acquisition sequence $SQ_{acq}$, applied successively to the pre-sequence $SQ_{pre}$, for acquiring MR signals.

In the pre-sequence $SQ_{pre}$, n-pieces (n≧2, for example, n=10) saturation pulses $SAT_1$ to $SAT_n$ each given a flip angle (FA) of 90° are applied at intervals concurrently with a slice gradient pulse $G_S$ (its strength $G_{s1}$). Each saturation pulse $SAT_1$ (to $SAT_n$) is formed by modulating a specified RF frequency carrier signal with a SINC function, for example. Assuming that a diagnostic region is set to the inferior limb as exemplified in FIG. 3, appropriate setting of, for example, the strength $G_{s1}$ of the slice gradient pulse $G_S$ enables a specified-thickness pre-saturated slice $A_{sat}$ to be determined at a substantially adjacent and parallel position to a desired objective imaging slice $A_{ima}$ in the inflowing side of arteries thereto. Thus each of the saturation pulses $SAT_1$ and $SAT_n$ is at intervals applied to the same pre-saturated slice $A_{sat}$.

Alternatively, when appropriately adjusting the strength of the slice gradient pulse $G_s$, the pre-saturated slice $A_{sat}$ is able to be set in the artery-outflowing side (i.e. vein-inflowing side) of the imaging slice $A_{ima}$. Between the imaging slice $A_{ima}$ and the pre-saturated slice $A_{sat}$, there may be a gap or gapless.

In the pre-sequence $SQ_{pre}$, immediately after the application of each saturation pulse $SAT_1$ (to $SAT_n$), gradient spoilers $SP_{s1}$ (to $SP_{sn}$), $SP_{r1}$ (to $SP_{rn}$), and $SP_{e1}$(to $SP_{en}$) for dephasing spins are applied in the slice, read-out, and phase-encoding directions, respectively.

Therefore, first, a pre-saturated slice Asat is slice-selected and excited by the first saturation pulse SAT1 and slice gradient pulse $G_S$, thereby the spins within the pre-saturated slice $A_{sat}$ including blood vessels (arteries and veins) are saturated. Spins remaining in the transverse x'-y' plane are dephased in each gradient application direction by the gradient spoiler $SP_{s1}$, $SP_{r1}$, and $SP_{e1}$ followed immediately. The combination of applying the saturation pulse and gradient spoilers is repeated n-times (for example, 10 times).

Since the pre-saturated slice $A_{sat}$ is spin-excited a plurality of times over a specified interval, even when the spins of blood whose flowing speed is relatively lower in the inferior limb or the like, the blood spins are steadily excited and saturated. Among the saturated spins, those in flows of the arteries are then carried into the imaging slice $A_{ima}$ to be reflected in an MR angiography image later reconstructed while those in flows of the veins just outflow from the pre-saturated slice $A_{sat}$ to the renal side and have no relation to the MR angiography image.

Following to the pre-sequence $SQ_{pre}$, under control of the sequencer 5, the pulses of a data acquisition sequence $SQ_{acq}$ are applied to the imaging slice $A_{ima}$. The sequence $SQ_{acq}$ is based on, for example, the FE method in which the strength of the slice gradient $G_s$ is set to $G_s=G_{s2}$ ($\neq G_{s1}$). Each signal received from the imaging slice $A_{ima}$ is processed into digital quantities in the receiver 8R, and stored in the arithmetic operation unit 10. Respondingly to an instruction sent from the controller 6, the unit 10 reconstructs an MRA (MR angiography) image by performing two-dimensional Fourier transform for a set of echo data mapped in a two-dimensional k (Fourier) space virtually formed in its memory.

While, by applying a plurality of saturation pulses in the pre-sequence $SQ_{pre}$, the arteries of adequately saturated spins inflow the imaging slice $A_{ima}$, the fresh (not-saturated) veins also inflow the imaging slice $A_{ima}$ from the opposite side to the pre-saturated slice $A_{pre}$, for example, the far side from the heart in the case of the inferior limb. Thus performing the data acquisition sequence $SQ_{acq}$ enables echo signal intensities acquired from the arteries to be very low and those acquired from the veins high.

Figure 4:
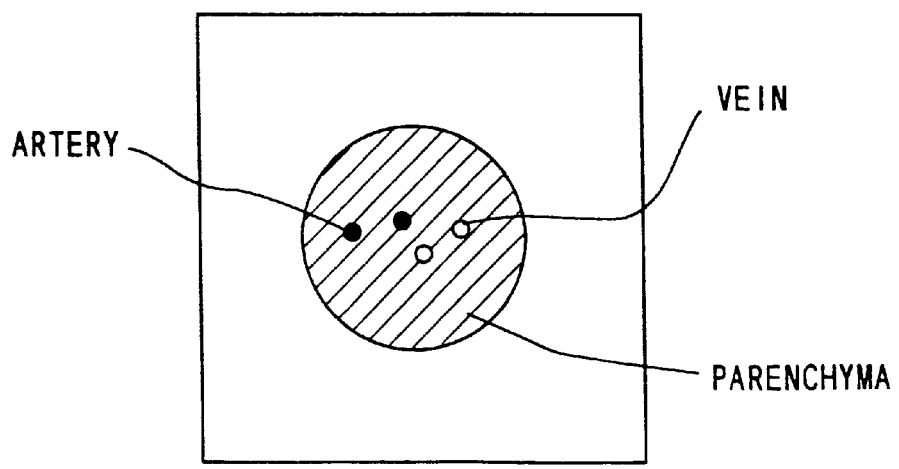
FIG. 4 is an example of an MRA image produced in the first embodiment.

As a result, in an MRA image reconstructed by the arithmetic operation unit 10, there is provided, as pictorially shown in FIG. 4, the marks of the arteries formed by reduction of pixel values due to reduction in signal intensities and the marks of the veins formed by receiving higher pixel intensities. It is therefore possible to visually separate the arteries and veins with each other in the image in a steady manner.

The embodiment employs a plurality of saturation pulses given a lower flip angle (90 degrees, as an example) applied to the same pre-saturated slice $A_{sat}$ at intervals. This means that the imaging slice $A_{ima}$ is repeatedly excited by the saturation pulses of a smaller flip angle at off-resonance of a given frequency offset. The parenchyma of the imaging slice $A_{ima}$ is almost stationary. In the case that the number n of all the saturation pulses is 10 and their flip angle FA is each 90 degrees, the parenchyma of the imaging slice $A_{ima}$ is subject to MT (magnetic transfer) effects corresponding to a total of 900 degrees (=90 degrees×10(=n)). Consequently the MR signal value from the parenchyma decrease.

By contrast, the veins flowing into the imaging slice Aima is smaller in MT effects receiving from the saturation pulses than the stationary parenchyma and its MT effects are suppressed into a minimum, since the blood is moving and the flip angle is divided into small ones (90 degrees, for example). For the arteries flowing into the imaging slice $A_{ima}$, the blood is flowing, which lowers MT effects, thus MT effects due to only one pulse of the flip angle FA=90 degrees becomes dominant. Hence, contrast between the vessels and parenchyma on a reconstructed MRA image increases greatly.

Furthermore, MRA images are provided without MR contrast medium in this embodiment, thus still keeping non-invasiveness of MR imaging. Compared with MR angiography using MR contrast medium, physical and mental endurance forced on patients are remarkably lowered by the improved MR angiography according to the invention.

(Second Embodiment)

A second embodiment of the invention will be described with reference to FIG. 5. The second embodiment relates to reduction in the number of applied the gradient spoiler pulses applied in the pre-sequence.

In this second embodiment and succeeding embodiments to it, the same or equivalent components as or to those of the MRI system in the above first embodiment are given the same references to omit or simplify explanation of constituent elements in this embodiment.

Figure 5:
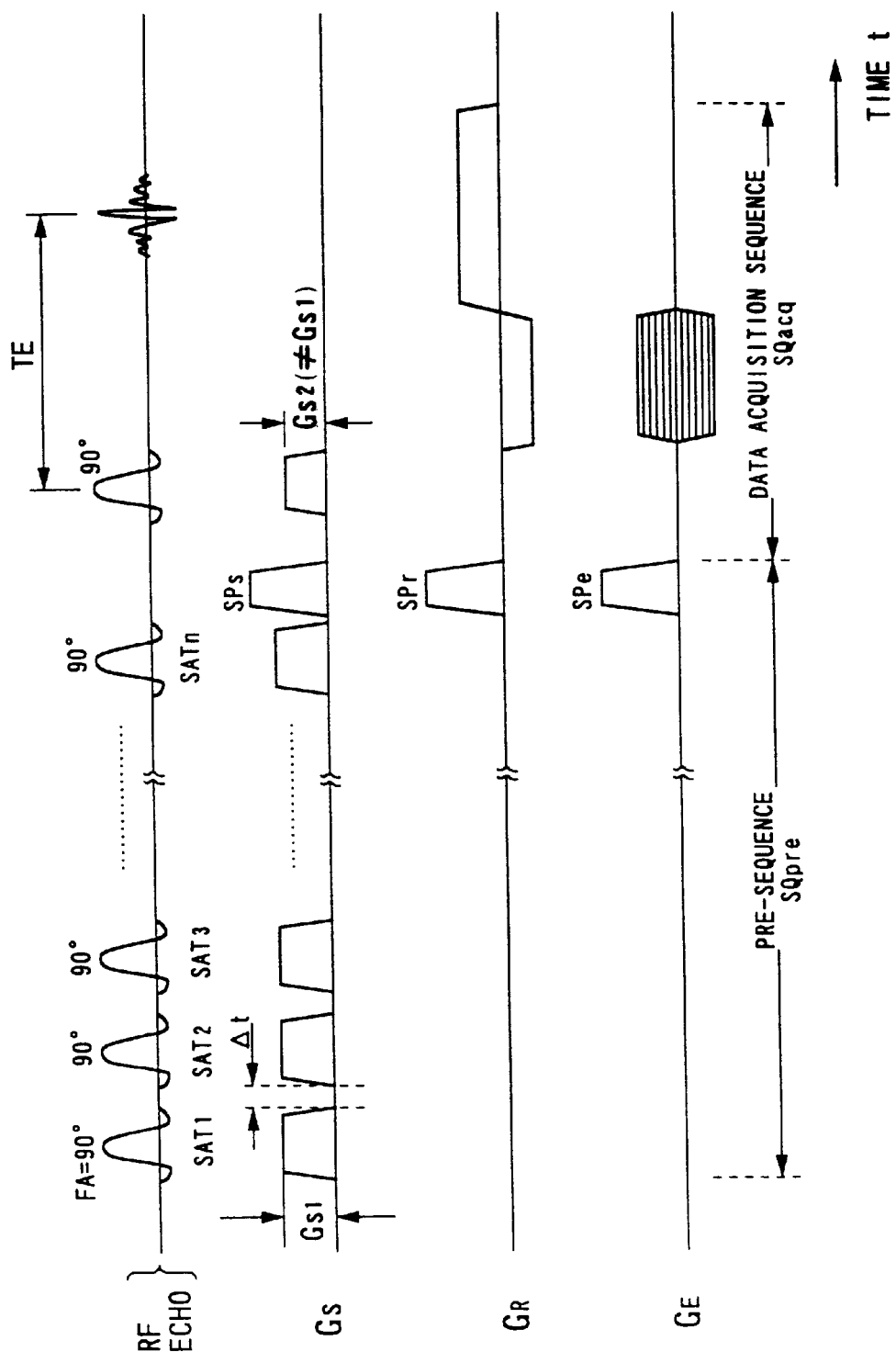
FIG. 5 is an example of a scan sequence to be executed in a second embodiment of the present invention.

The sequencer 5 of the MRI system according to the invention executes a scan sequence shown in FIG. 5 for imaging.

The scan sequence in FIG. 5 includes, in the same way as in the first embodiment, a pre-sequence $SQ_{pre}$ and a data acquisition sequence $SQ_{acq}$. In comparison with the first embodiment, while the data acquisition sequence $SQ_{acq}$ is set to be the same, the pre-sequence $SQ_{pre}$ differs in the number of the gradient spoiler pulses. Specifically, in the pre-sequence $SQ_{pre}$, a plurality of n-piece saturation pulses $SAT_1$ to $SAT_n$ all of which has a flip angle FA of 90 degrees are sequentially applied at an interval of $\Delta t$ with the slice gradient $G_s$=strength $G_{s1}$. Only one gradient spoiler pulse is individually applied, as an end spoiler, in the slice, read-out, and phase-encoding directions after the temporal last one in a train of the n-piece saturation pulses has been applied. The data acquisition sequence $SQ_{acq}$ follows the gradient spoiler pulses applied only one time in each direction.

By applying only one gradient spoiler pulse $SP_s(SP_r, SP_e)$ in each direction at the end of the pre-sequence $SQ_{pre}$ unnecessary spins which is present in the transverse magnetization and will flow into an imaging slice $A_{ima}$ afterward, and/or remain in the imaging slice $A_{ima}$ (spins of parenchyma and blood) are fully dephased, thus suppressing artifacts in the objective imaging slice. This provides a time-saving and effective application method of the gradient spoiler pulses, based on a viewpoint that dephasing is not necessarily required every time of applying the saturation pulse because the blood usually flows.

According to the second embodiment, it is therefore possible to provide the same or equivalent advantages as or to the first embodiment, and additionally to shorten the application interval necessary for the pre-sequence. Hence, in an MRA image, a higher contrast between the parenchyma and blood can be maintained and the arteries and veins can be separated without fail. A reliable, high-quality MRA image is non-invasively provided in a faster scan speed.

(Third Embodiment)

A third embodiment of the invention will be explained with reference to FIGS. 6 and 7. A feature of the third embodiment is that the flip angle of the saturation pulses is variable.

Figure 6:
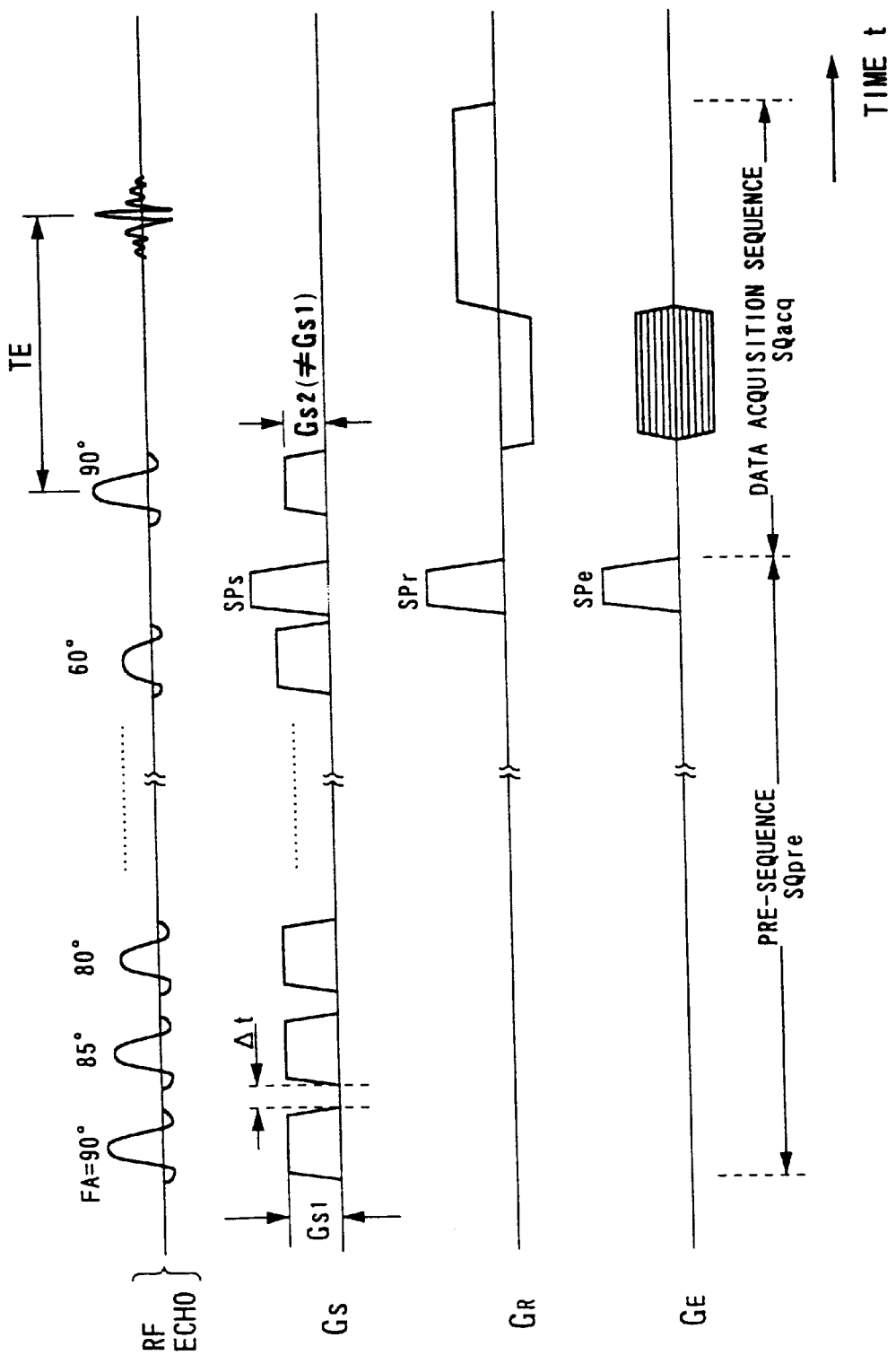
FIG. 6 is an example of a scan sequence to be executed in a third embodiment of the present invention.

The sequencer 5 of the MRI system of the invention is designed to execute a scan sequence for imaging shown in FIG. 6.

Like the first embodiment, the scan sequence of FIG. 6 includes a pre-sequence $SQ_{pre}$ and a data acquisition sequence $SQ_{acq}$. Comparing with that in the first embodiment, the data acquisition sequence $SQ_{acq}$ is determined in the same manner, but the pre-sequence $SQ_{pre}$ differs in the number of the gradient spoiler pulses. Additionally, a plurality of n-piece saturation pulses $SAT_1$ to $SAT_n$ whose flip angles are changed for each pulse are in sequence applied at an interval of $\Delta t$ with the slice gradient of strength $G_{s1}$. After the temporal saturation pulse SATn has been finished, the gradient spoiler pulse individually applied just one time in the slice, read-out, and phase-encoding directions, respectively. The gradient spoiler pulse thus-applied is followed by the data acquisition sequence $SQ_{acq}$, like the previous embodiments.

The flip angles FA for the plurality of n-piece saturation pulses $SAT_1$ to $SAT_n$ are determined, as an example, such that FA=90° for the first pulse, FA=85° for the second one, FA=80° for the third one, . . . , and FA =60° for the last one by selecting a gradually decreasing flip angle system. The decreasing flip angle system is selected based on the following reason.

Figure 7:
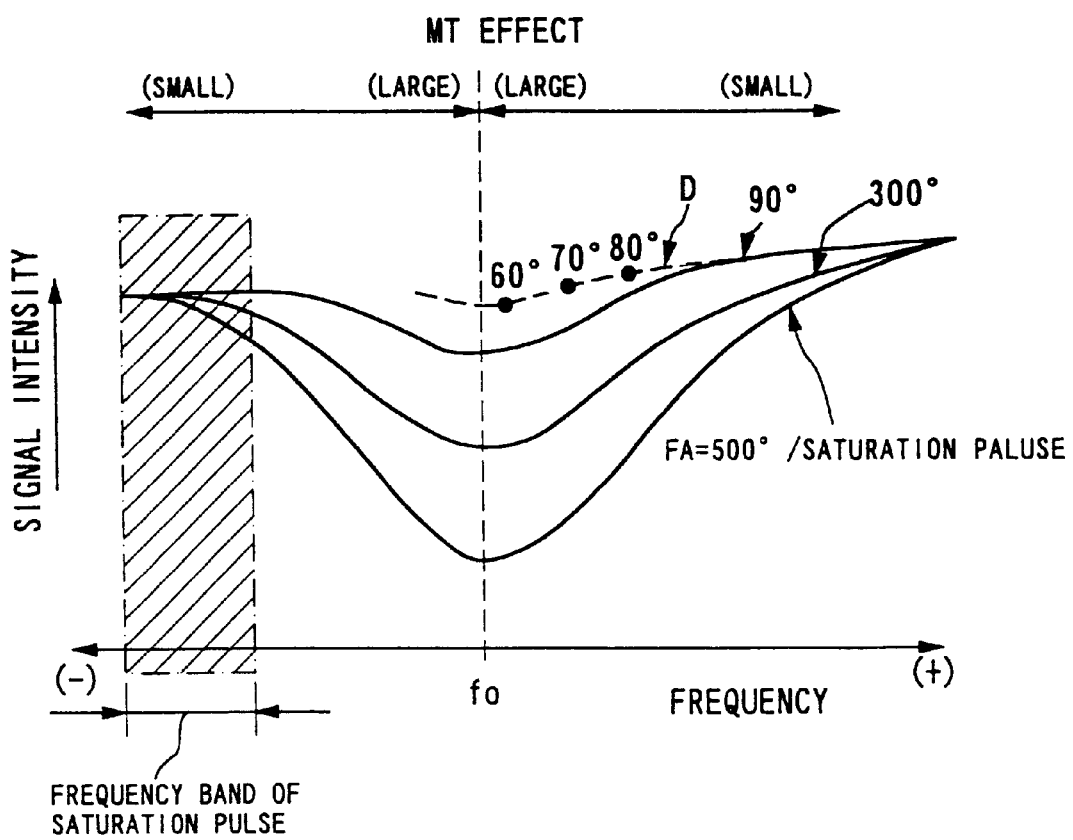
FIG. 7 explains the relation between changes in the MT effect in association with changes in flip angle.

A graph in FIG. 7 shows changes in signal intensities, with a flip angle FA per one saturation pulse taken as a parameter, when resonance frequencies of spins (corresponding to slice positions) is set to the axis of abscissa and MR signals to the axis of ordinates. A frequency $f_0$ in the axis of abscissa is a resonant frequency (enter frequency) of water at the slice-directional center in an objective imaging slice. As figured out from this graphical illustration, the signal intensities decreases, i.e., MT (magnetization transfer) effects increases, as the frequency approaches near to the center frequency and the flip angle FA becomes larger.

Therefore, the flip angle control manner by which the flip angle FA is gradually decreased in a train of saturation pulses leads to thefact that the MT effect influencing on the vein (refer to FIG. 3) flowing into the imaging slice $A_{ima}$ will weaken (decrease) as positions arbitrarily specified in the stream of the vein approach to the center frequency $f_0$ (i.e., the position of the imaging slice). This state can pictorially be shown in FIG. 7 by a curve D branching from the curve of the flip angle FA=90°. The curve D is illustrated in a condition that the frequency band of the saturation pulses positions in the negative side on the axis of the abscissa. Thus a reduction in the MR signal emanating from a flow of blood flowing into the imaging slice $A_{ima}$ from the side opposite to the pre-saturated slice $A_{sat}$ (veins herein) is caused to be suppressed to a minimum, thereby becoming a relatively higher signal intensity.

In contrast, the parenchyma of the imaging slice $A_{ima}$ causes a greater proportion of MT effects, because it is excited in off-resonance with a certain frequency offset corresponding to a difference in slice positions to the pre-saturated slice Asat to which a plurality of n-piece saturation pulses are applied, thus providing the lowered MR signal intensity.

In the MRI system of the third embodiment, in addition to the same or equivalent functions and advantages as or to that in the second embodiment, the contrast between the parenchyma and blood flows in an imaging slice is remarkably enhanced, supplying a superior MRA image in both image quality and visibility.

In the third embodiment, alternatively, the flip angles for a plurality of saturation pulses may be changed in an order of, for example, 90°, 90°, 80°, 80°, . . . , 60°, and 60° on the time-series basis.

Alternatively, as one variation, when vessels outflowing from an objective imaging slice need to be enhanced with regard to their saturation effects, the flip angles for a plurality of saturation pulses are changed in an order of, for example, 60°, 65°, 70°, 75°, . . . , 85°, and 90° on the time-series basis, like gradually increasing.

(Fourth Embodiment)

A fourth embodiment of the invention will be explained using FIG. 8. An MRI system of the fourth embodiment relates to further improvement in the scan sequence of the foregoing second embodiment, and in particular, to shortening time required for performing the pre-sequence $SQ_{pre}$.

Figure 8:
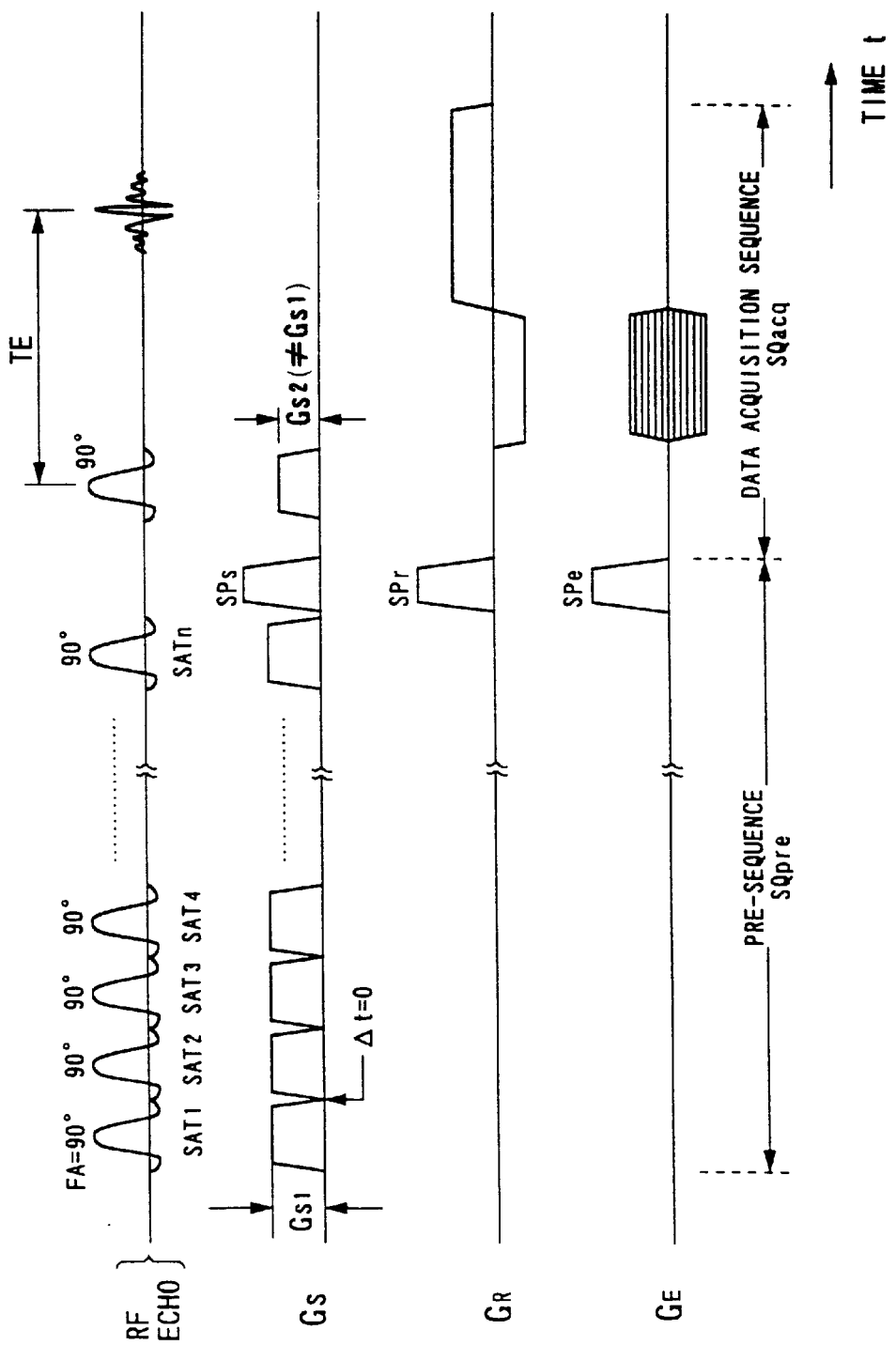
FIG. 8 is an example of a scan sequence to be executed in a fourth embodiment of the present invention.

FIG. 8 shows a scan sequence employed in the MRI system of this embodiment. As illustrated therein, the scan sequence uses the pre-saturated sequence $SQ_{pre}$ as a saturation sequence, where although the saturation pulses $SAT_1$ to $SAT_n$ are slice-selective applied to a pre-saturated slice $A_{sat}$, a plurality of slice gradient pulses $G_s$ applied concurrently with the saturation pulses is continuous, without time gaps. This continuous pulse configuration excludes the time interval $\Delta t$ set between the pulses described in foregoing each embodiment.

Thus time necessary for applying a plurality of n-piece saturation pulses $SAT_1$ to $SAT_n$ can be shortened in total by "$\Delta t (n-1)$", thus an imaging time for MR angiography being shortened correspondingly.

(Fifth Embodiment)

A fifth embodiment of the embodiment will be described with reference to FIG. 9. In an MRI system of this embodiment, the scan sequence shown in the fourth embodiment are yet improved in terms of viewpoints of time saving in a pre-sequence $SQ_{pre}$ and reduction in load for switching the slice gradient $G_s$.

Figure 9:
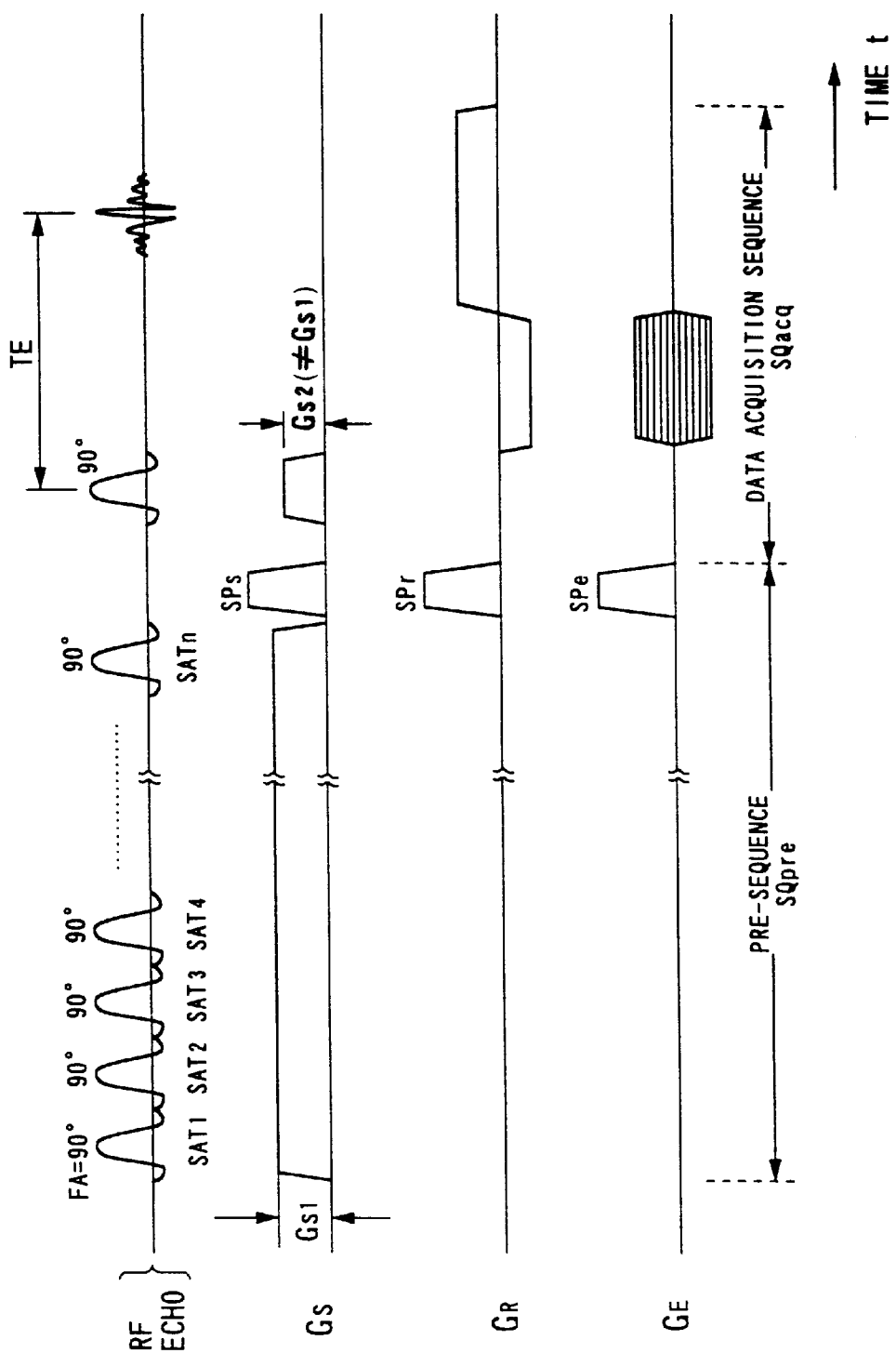
FIG. 9 is an example of a scan sequence to be executed in a fifth embodiment of the present invention.

FIG. 9 shows a scan sequence adopted in the MRI system of this embodiment. As represented in the pre-sequence $SQ_{pre}$ of the scan sequence, the slice gradient $G_s$ is determined to be continuously applied, as one pulse, concurrently with an application interval of a plurality of n-piece saturation pulses $SAT_1$ to $SAT_n$.

Like the fourth embodiment, on top of the time-shortening of approximate "$\Delta t (n-1)$" depending on an interval set between the slice gradient pulses, time pieces $\Delta ts$ (for example, 0.6 to 1 msec) for slue rates of each slice gradient pulse $G_s$ are also unnecessary. In other words, it is possible to further shorten a time of approximate "$\Delta ts (2n-2)$".

As a result, an imaging time for MR angiography is also shortened and switching loads for on-off repetition of the slice gradient $G_s$ at an extremely short interval are reduced, thus requirements for switching characteristics of the gradient power supply 4 and x-, y-, and z-coil 3x, 3y, and 3z being lowered, thus leading to easier design.

(Sixth Embodiment)

A sixth embodiment of the present invention will be described in conjunction with FIG. 10. An MRI system of this embodiment provides a feature that a saturation sequence including a plurality of saturation pulses, inherent to the invention, is combined into a fast FLAIR (Fluid Attenuated Inversion Recovery) imaging method.

Figure 10:
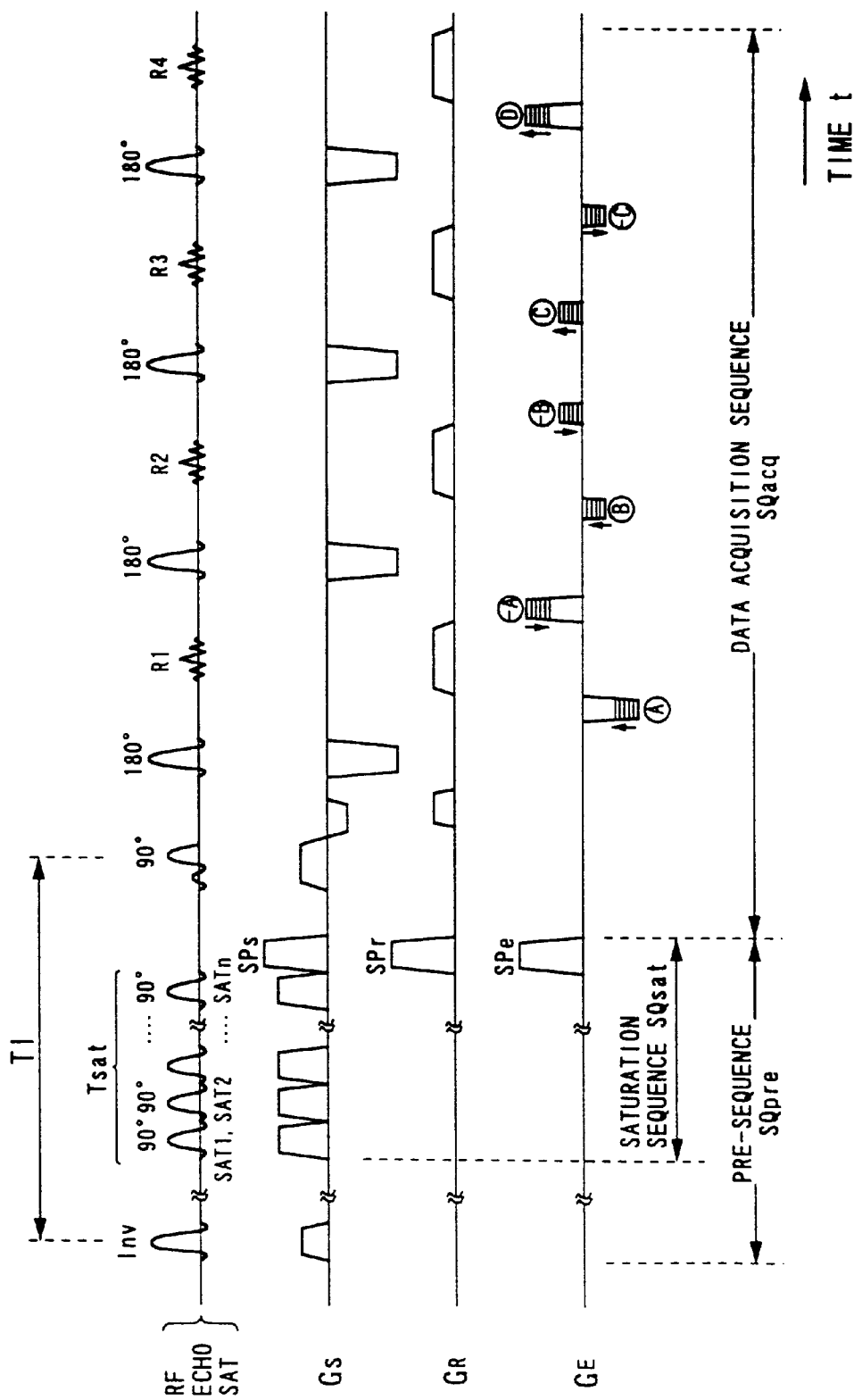
FIG. 10 is an example showing a single slice type of scan sequence depending on fast FLAIR method, which is executed in a sixth embodiment of the present invention.

As shown in FIG. 10, a scan sequence employed by the embodiment MRI system, which is for single slice imaging, consisting of a pre-sequence $SQ_{pre}$ including an inversion pulse Inv and a saturation sequence $SQ_{sat}$ and a data acquisition sequence $SQ_{acq}$ constructed by a fast SE (FSE) method (also referred to as RARE method). Among them, the inversion pulse Inv and fast SE method-based data acquisition sequence $SQ_{acq}$ constitutes the fast FLAIR method sequence. The fast SE method of this embodiment is designed on a known PASTA (Polarity altered spectral and spatial selective acquisition) method (for example, refer to "SMR 1995 #657 "A Polarity Altered Spectral and Spatial Selective Acquisition Technique"").

Alternatively, the data acquisition sequence $SQ_{acq}$ may be configured using a well-known normal SE method sequence, thus forming a FLAIR sequence, where the pulses of the saturation sequence inherent to the invention is combined with the FLAIR method.

The saturation sequence $SQ_{sat}$, as shown in FIG. 10, is a pulse train carried out as part of the pre-sequence $SQ_{pre}$ and consists of a saturation pulse train $T_{sat}$ and gradient spoiler pulses $SP_s$, $SP_r$, and $SP_e$. This saturation sequence $SQ_{sat}$ is the same as the foregoing fourth embodiment in construction.

Figure 3:
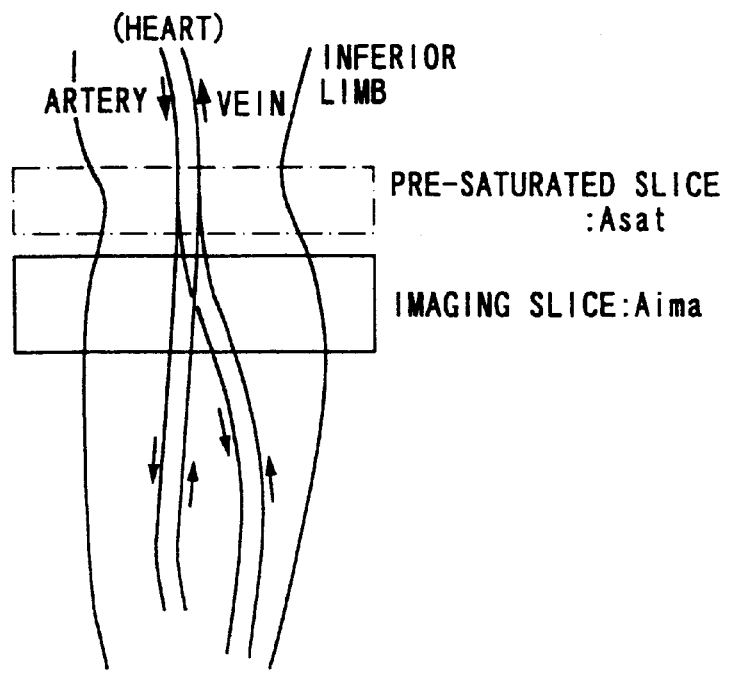
FIG. 3 is an example illustratively showing an objective imaging slice, pre-saturated slice, and blood vessels running therethrough.

According to the scan sequence, first, the inversion pulse Inv and slice gradient pulse $G_s$ are concurrently applied to an objective imaging slice $A_{ima}$ (refer to FIG. 3). The inversion pulse Inv is formed, for example, an 180° RF pulse. The inversion pulse Inv is applied by the transmitter 8T via the RF coil 7, while the slice-selective gradient $G_s$ is applied by the gradient power supply 4 via the gradient coils 3z, 3z the strength of the gradient Gs is set to select an objective imaging slice.

When the application of the inversion pulse Inv comes to an end, the fast FLAIR sequence provides a standby state established by a desired inversion time (delay time) TI. In this embodiment, utilizing the period of the inversion time TI, the saturation sequence $SQ_{sat}$ consisting of the saturation pulse train $T_{sat}$ and the gradient spoiler pulses $SP_s$, $SP_r$, and $SP_e$ is executed, as shown in the figure, during the interval of TI. The saturation pulse train $T_{sat}$, like the above, is formed by having a plurality of saturation pulses $SAT_1$, $SAT_2$, . . . , $SAT_n$ and a plurality of slice gradient pulses $G_s$ applied in parallel with the saturation pulses.

Carrying out the saturation sequence $SQ_{sat}$, like the above, enables the spins of blood passing a pre-saturated slice $A_{sat}$ (refer to FIG. 3) to be saturated and an objective imaging slice $A_{ima}$ to cause MT effects therein due to off-resonance excitation.

When the inversion time TI coming to an end, the data acquisition sequence $SQ_{acq}$ based on the fast SE method utilizing the PASTA technique is performed for the imaging slice $A_{ima}$ wherein the spins have been inverted and excited by the inversion pulse Inv.

Specifically, a 90° RF pulse is applied together with a slice-selective gradient $G_s$ initially. The 90° RF pulse is formed to have a narrow frequency band to frequency-selective excite proton spins of water alone. Consequently, the imaging slice $A_{ima}$ of a patient body is selected, and only spins of protons of water in the slice are excited and flipped onto a y'-axis (rotational coordinates). A slice-selective gradient $G_S$ is then polarity-inverted to be a rephase pulse. Thereafter, a read-out gradient $G_R$ is applied via the gradient coils 3x. This is intended to phase spins arranged in the $G_R$ direction in the slice $A_{ima}$ at time instants coincident with the middles of productions of echoes.

A first wider-frequency-band 180° RF pulse is then applied together with a polarity-altered slice-selective gradient Gs. This causes the spins of protons to rotate 180° about the y'-axis. Namely refocusing is caused for only proton spins of water. Moreover, after a first phase-encoding gradient $G_E(=A)$ is applied to the patient P by the gradient power supply 4 via the gradient coils 3y, a first spin echo R1 is acquired via the RF coil 7 along with the application of a read-out gradient $G_R$ via the gradient coils 3x.

Thereafter, a phase-encoding gradient $G_E(=-A)$ of opposite polarity is applied. This is intended to return an encoding position to a center position (ke=0) in a phase-encoding direction in a k-space on application of a 180° RF pulse and to eventually avoid deterioration of image quality due to stimulated echoes.

Like the first refocusing, a second 180° RF pulse is then applied together with a slice-selective gradient $G_s$. Thereafter, a second phase-encoding gradient $G_E(=B)$ is applied. A second spin echo R2 is then acquired via the RF coil 7 along with the application of a read-out gradient $G_R$.

Likewise, third and fourth spin echoes R3 and R4 are acquired.

These kinds of processing are repeatedly executed for each phase-encoding amount at interval of a certain repetition time TR.

Echoes produced by single slice scan and mostly of proton spins of water are sent consecutively to the receiver 8R. After subjected to such processing as amplification, intermediate-frequency transform, phase detection, and low-frequency amplification, the echoes are converted into a digital form and thus recomposed into echo data. The echo data is mapped into a memory area corresponding to a k-space, in which Fourier transform can be performed, by the arithmetic unit 10. Two-dimensional Fourier transform is then performed to reconstruct an MRA image in a real space. This image is stored in the memory unit 13 and displayed on the display unit 14.

As described above, even when employing the saturation sequence $SQ_{sat}$ in the fast FLAIR method can offer the equivalent functions and features to those described in the foregoing embodiments, in addition to particular advantages that increases the number of slices and visually-separates arteries and veins from each other, which result from the fast FLAIR technique. Further, incorporating a pulse train of the saturation sequence $T_{sat}$ into the inversion time TI prevents the whole scan time from being longer. Still further, this embodiment widens applicable data acquisition sequences and enhances versatility of the saturation sequence. Moreover, thanks to the PASTA technique, suppressions effect for echo signals induced from fat is also available.

(Seventh Embodiment)

A seventh embodiment of the invention will now be described in conjunction with FIGS. 11 to 13. An MRI system described herein uses a saturation sequence including a plurality of saturation pulses of the invention combined in the fast FLAIR sequence, like the sixth embodiment, which is carried out by multislice scan based on a nesting mode.

Figure 11:
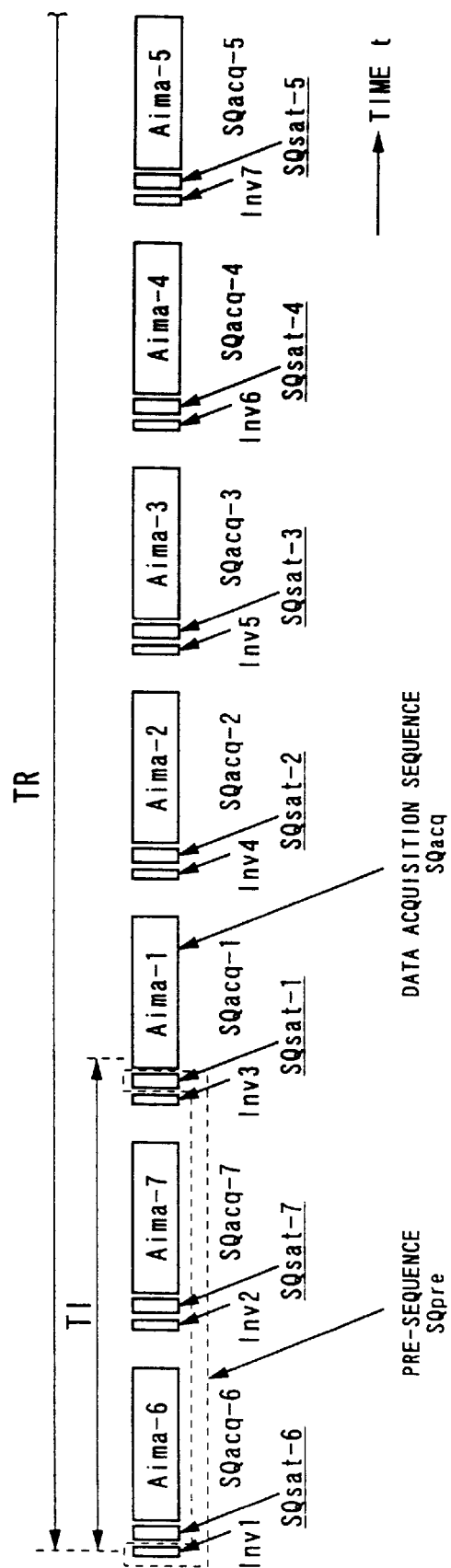
FIG. 11 is an example showing a multislice type of scan sequence depending on fast FLAIR method, which is executed in a seventh embodiment of the present invention.

FIG. 11 outlines a whole scan sequence carried out by a multislice technique in which the fast FLAIR sequence according to the invention is build up based on sequential-mode nesting. FIG. 12 shows a correspondence between the scan sequence and multi-sliced positions. FIG. 13 details the beginning part of the scan sequence.

Figure 12A:
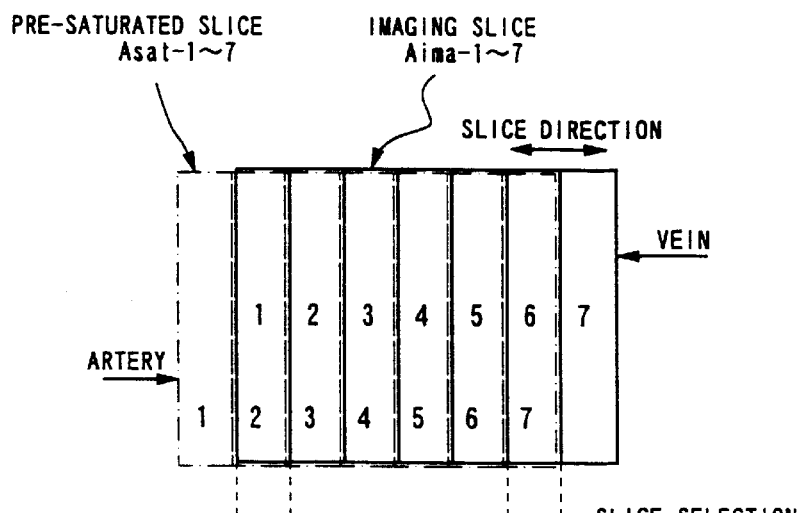
FIGS. 12A and 12B exemplify the relation between the scan sequence and multiscale positions in the seventh embodiment.
Figure 13:
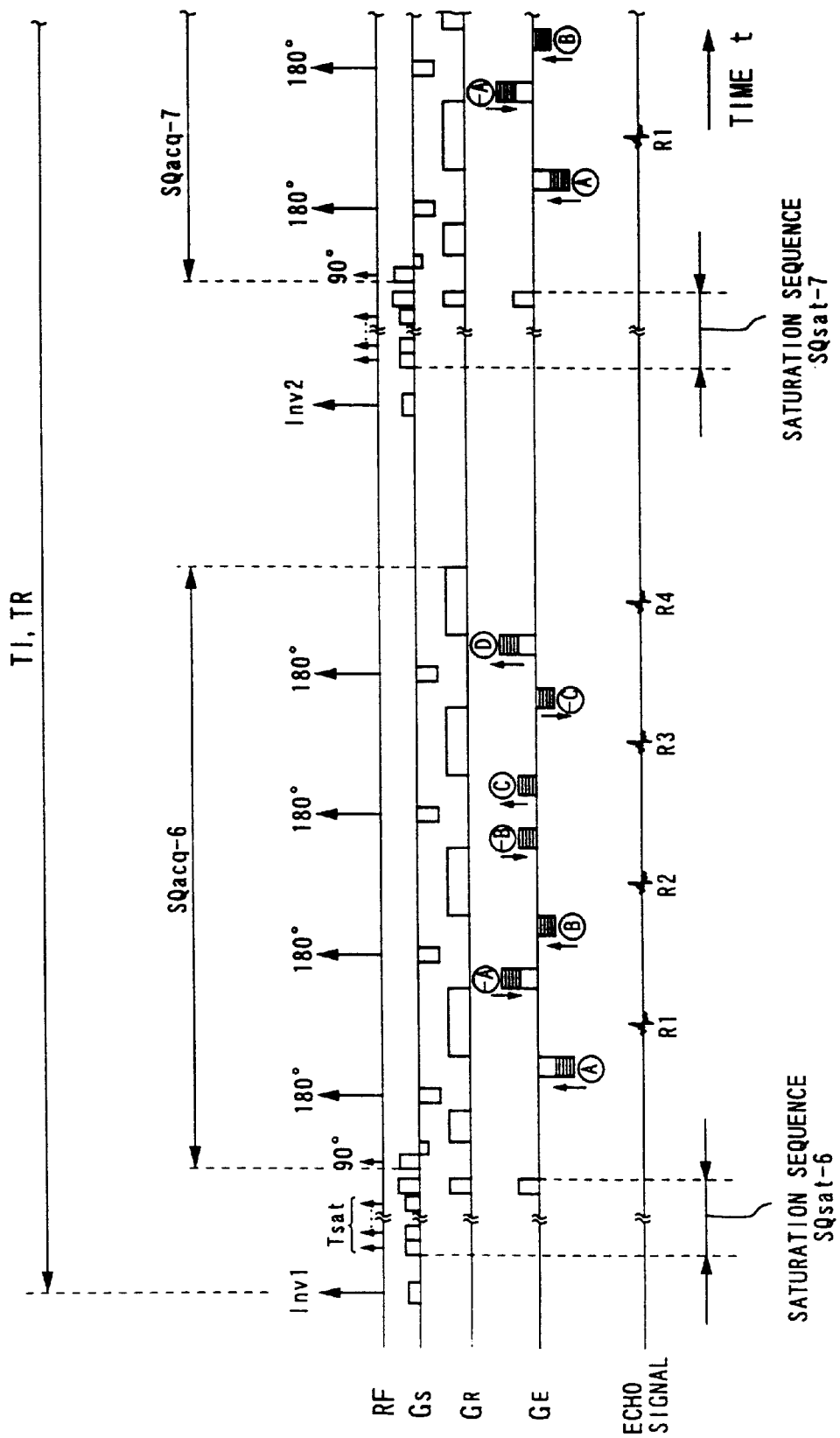
FIG. 13 is a train of pulses representing in detail the beginning of the scan sequence illustratively shown in FIG. 11.

FIG. 12A pictorially exemplifies a combination of multi-sliced seven adjoining imaging slices $A_{ima-1}$ to $A_{ima-7}$ of an examined region of a patient and seven pre-saturated slice $A_{pre-1}$ to $A_{pre-7}$ each specified correspondingly to each imaging slice.

Figure 12B:
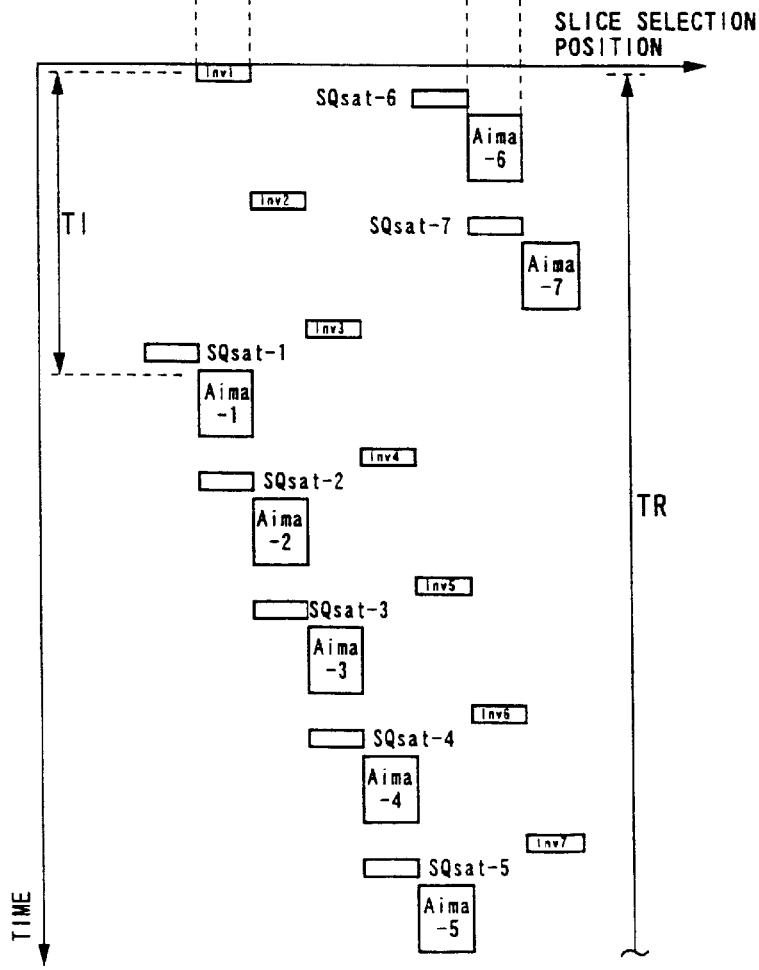

FIGS. 11 and 12B show an example of a nested pulse sequence resulting from sequential-mode nesting. The sequence uses seven inversion pulses Inv1 to Inv7 and seven corresponding data acquisition sequences (imaging sequences) Imaging1 to Imaging7, which constitute the fast FLAIR technique, and during the inversion time TI produced after each inversion pulse Inv has been applied to each imaging slice, further inversion pulses Inv, saturation sequences $SQ_{sat}$, and PASTA-based data acquisition sequences $SQ_{acq}$, each pulse and sequence being set for two imaging slices $A_{ima}$, are performed sequentially to avoid the entire scan time from being elongated. A combination of the inversion pulse Inv and saturation sequence $SQ_{sat}$ for each imaging slice constitutes the pre-sequence according to the invention.

The inversion pulse Inv, saturation sequence $SQ_{sat}$, and data acquisition sequence $SQ_{acq}$ for each imaging slice are formed in the same way as those described in FIG. 10.

According to this sequential-mode nesting scan, first, an inversion pulse Inv1 is applied to a first imaging slice $A_{ima}$. After a given time from this, a saturation sequence $SQ_{sat-6}$ is performed on a pre-saturated slice $A_{pre-6}$ corresponding to an imaging slice $A_{ima-6}$ to which an inversion pulse Inv6 was applied. And after a given time, a data acquisition sequence $SQ_{acq\ -6}$ is performed on the imaging slice $A_{ima-6}$.

After a given time, an inversion pulse Inv2 is applied to a second imaging slice $A_{ima-2}$. After a given time from this, a saturation sequence $SQ_{sat-7}$ is performed on a pre-saturated slice $A_{pre-7}$ corresponding to an imaging slice $A_{ima-7}$ to which an inversion pulse Inv7 was applied. And after a given time, a data acquisition sequence $SQ_{acq-7}$ is performed on the imaging slices $A_{ima-7}$.

Further, after a given time, an inversion pulse Inv3 is applied to a third Imaging slices $A_{ima-3}$. After a given time from this, a saturation sequence $SQ_{sat-1}$ is performed on a pre-saturated slice $A_{pre-1}$ corresponding to an imaging slice $A_{ima-1}$ to which an inversion pulse Inv6 was applied above. And after a given time, a data acquisition sequence $SQ_{acq-1}$ is performed on the imaging slice $A_{ima-1}$.

Further, after a given time, an inversion pulse Inv4 is applied to a fourth imaging slice $A_{ima-4}$ Thereafter, application of pulses and acquisition of MR signals is performed in the same manner, and finally, a data acquisition sequence $SQ_{act-5}$ is performed on a fifth imaging slice $A_{ima-5}$. Thus a repetition time TR elapses.

Therefore, this imaging can be done with advantages of the fast FLAIR technique. The entire scan time can only depend on that in the fast FLAIR sequence, eliminating the necessity of elongating the scan time.

(Eighth Embodiment)

An eighth embodiment of the invention will now be described in conjunction with FIG. 14. An MRI system described herein uses another mode of nesting in the scan sequence described in the seventh embodiment; that is an interleave-mode.

In the MRI system, construction and functions other than the nesting mode are the same as those in the seventh embodiment.

Figure 14:
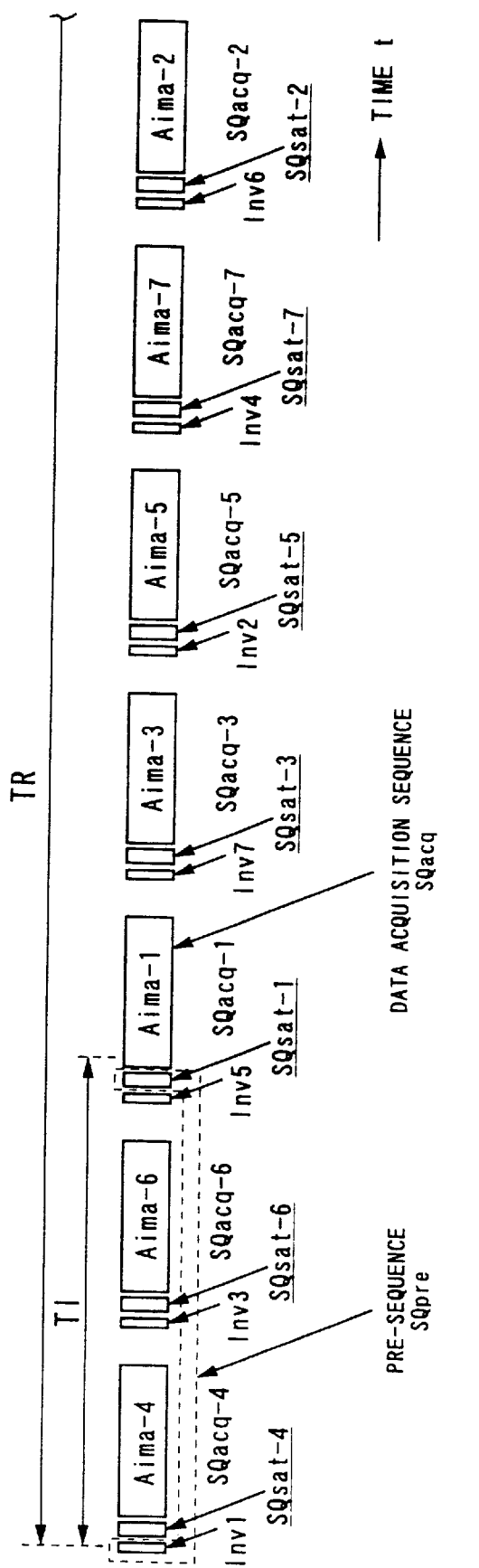
FIG. 14 is an example showing a multislice type of scan sequence depending on fast FLAIR method, which is executed in an eighth embodiment of the present invention.

Referring to an interleave-mode nesting scan sequence shown in FIG. 14, first, an inversion pulse Inv1 is applied to a first imaging slice $A_{ima-1}$. After a given time from this, a saturation sequence $SQ_{sat-4}$ is performed on a pre-saturated slice $A_{pre-4}$ corresponding to an imaging slice $A_{ima-4}$ to which an inversion pulse Inv4 was previously applied. And after a given time, a data acquisition sequence $SQ_{acq-4}$ is performed on the imaging slice $A_{ima-4}$.

After a given time, an inversion pulse Inv3 is applied to a third imaging slice $A_{ima-3}$. After a given time from this, a saturation sequence $SQ_{sat-6}$ is performed on a pre-saturated slice $A_{pre-6}$ corresponding to an imaging slice $A_{ima-6}$ to which an inversion pulse Inv6 was previously applied. And after a given time, a data acquisition sequence $SQ_{acq-6}$ is performed on the imaging slice $A_{ima-6}$.

After a given time, an inversion pulse Inv5 is applied to a fifth imaging slice $A_{ima-5}$ After a given time from this, a saturation sequence $SQ_{sat-1}$ is performed on a pre-saturated slice $A_{pre-1}$ corresponding to an imaging slice $A_{ima-1}$ to which an inversion pulse Inv1 was applied. And after a given time, a data acquisition sequence $SQ_{acq-1}$ is performed on the imaging slice $A_{ima-1}$.

Further after a given time, an inversion pulse Inv7 is applied to a seventh imaging slice $A_{ima-7}$. Thereafter, application of pulses and acquisition of MR signals is performed in the same manner, and finally, a data acquisition sequence $SQ_{acq-2}$ is performed on a second imaging slice $A_{ima-1}$. Thus a repetition time TR elapses.

Accordingly, for the same multislice sequence based on the fast FLAIR technique as that described in the seventh embodiment, the imaging slice can be selected every two slices, such as $A_{ima-4}$, $A_{ima-6}$, $A_{ima-1}$, $A_{ima-5}$, $A_{ima-7}$, etc. Thus, additionally to the advantages obtained in the seventh embodiment, some other advantages are provided such that interaction of spins between imaging slices can surely be excluded to increase image quality.

In the foregoing embodiments, the slice-selective position of the pre-saturated slice $A_{pre}$ is arbitrarily determined. For example, the slice $A_{pre}$ can be set at the outflowing side of arteries (i.e., the inflowing side of veins) to the imaging slice $A_{ima}$ (refer the lower side of the slice $A_{ima}$ in FIG. 3). In this case, although the relation in signal strength becomes opposite between the arteries and veins, there is provided an MRA image in which arteries and veins are still visually well-separated and a higher contrast between vessels and parenchyma is maintained.

Further, in the foregoing embodiments, the gradient spoiler pulse may be applied in selected one or two gradient-applying directions only.

Still further, the saturation pulse is not limited to the 90-degrees RF pulse that uses the SINC function, but a variety of pulses may be used, provided that it can pre-excite a slice including flows of blood making inflow to an objective imaging slice. For example, the saturation pulse may be of a binomial pulse.

It may also be possible that the pre-saturated slice be positioned by changing the bandwidth of an excitation RF pulse with the strength of the slice gradient unchanged.

Although the description above contains many specificities, these should not be construed as limiting the scope of the invention but as merely providing illustrations of some of the presently preferred embodiments of this invention. Thus the scope of this invention should be determined by the appended claims and their equivalents.

What is claimed is:

1. A magnetic resonance system obtaining an MR (magnetic resonance) angiography image of an imaging slice of a subject, comprising:

first means for performing a pre-sequence including a plurality of saturation pulses applied sequentially in time to the same pre-saturated slice of the subject which is positionally different from the imaging slice, said plurality of saturation pulses providing an MT effect, second means for thereafter performing a data acquisition sequence for acquiring MR signals from the imaging slice after the performance of the pre-sequence; and means for repeatedly operating said first and second means in succession and for producing an angiography image based on acquired MR signals.

2. The system of claim 1, wherein the pre-sequence include at least one slice gradient pulse applied in parallel with the plurality of saturation pulses, the gradient pulse being used for determining a spatial position of the pre-saturated slice differently from a spatial position of the imaging slice.

3. The system of claim 2, wherein the slice gradient pulse includes a plurality of slice gradient pulses, each applied in parallel with a corresponding one of the plurality of saturation pulses.

4. The system of claim 3, wherein the plurality of saturation pulses are juxtaposed in a time axis direction without a temporal gap between adjacent ones of the saturation pulses.

5. The system of claim 2, wherein the at least one slice gradient pulse consists of a single slice gradient pulse applied in parallel with all the plurality of saturation pulses.

6. The system of claim 2, wherein the pre-sequence includes a plurality of gradient spoiler pulses, a spoiler pulse being applied to the subject after each of the saturation pulses.

7. The system of claim 2, wherein the pre-sequence includes at least one gradient spoiler pulse applied to the subject for a first time after the plurality of saturation pulses have been applied.

8. The system of claim 7, wherein the at least one gradient spoiler pulse includes at least a gradient spoiler pulse applied in a slice direction common with the imaging slice.

9. The system of claim 7, wherein the at least one gradient spoiler pulse includes three gradient spoiler pulses applied in three directions, respectively:

a slice direction common with the imaging slice, and phase-encoding and read-out directions perpendicular to the slice direction.

10. The system of claim 2, wherein each of the plurality of saturation pulses causes a magnetic spin in the pre-saturated slice to turn at a flip angle of less than 100 degrees.

11. The system of claim 2, wherein at least one of the plurality of saturation pulses causes a magnetic spin in the pre-saturated slice to turn at a flip angle that is different from that caused by another of the saturation pulses.

12. The system of claim 11, wherein each of the plurality of saturation pulses causes a magnetic spin in the pre-saturation slice to turn at a flip angle that is different from all others of the saturation pulses.

13. The system of claim 12, wherein the flip angle of each of the plurality of saturation pulses successively lowers gradually as successive saturation pulses are applied.

14. The system of claim 2, wherein the slice gradient defines the pre-saturated slice substantially in parallel with the imaging slice.

15. The system of claim 2, wherein the data acquisition sequence includes a pulse train constituting part of a fast FLAIR (Fluid Attenuated Inversion Recovery) sequence in which an inversion pulse is first applied before a pulse train applied after an inversion time from the application of the inversion pulse.

16. The system of claim 15, wherein the first means is constructed to perform the pre-sequence during the inversion time interval.

17. The system of claim 16, wherein the first and second means repeat the pre-sequence and the data acquisition sequences based on a multislice technique.

18. The system of claim 17, wherein the first and second means repeat both the pre-sequence and the data acquisition sequence in an interleaved mode for obtaining image data for each of a plurality of image slices.

19. A magnetic resonance imaging system for obtaining an MR (magnetic resonance) angiography image of an imaging slice of a subject, said system comprising:

a magnet for generating a static magnetic field into a space in which the subject is placed;

a gradient generation unit for generating via gradient coils slice, phase-encoding, and read-out magnetic gradients superimposed on the static magnetic field;

a transmission/reception unit including an RF coil transmitting to the subject a spin-exciting RF signal and receiving MR signals emanated from the subject;

a reconstruction unit for reconstructing the image based on the MR signals received by the reception unit; and a sequencer for performing a scan sequence of pulses through control of the gradient generation unit and the transmission/reception unit, wherein the scan sequence of pulses is formed for sequentially producing:

a pre-sequence including a plurality of saturation pulses applied sequentially in time to the same pre-saturated slice which is positionally different from the imaging slice concurrently with at least a slice gradient pulse for slice-selecting the pre-saturated slice, said plurality of saturation pulses providing an MT effect; and a data acquisition sequence applied to the imaging slice, after application of the pre-sequence for acquiring MR signals from the imaging slice.

20. A method of imaging obtaining an MR (magnetic resonance) angiography image of an imaging slice of a subject, said method comprising:

first, performing a pre-sequence including a plurality of saturation pulses applied sequentially in time to the same pre-saturated slice which is selected to be positionally different from the imaging slice said plurality of saturation pulses providing an MT effect;

second, thereafter performing a data acquisition sequence for acquiring MR signals from the imaging slice; and producing the angiography image using the acquired MR signals.

21. The system of claim 19, wherein the at least one slice gradient pulse includes a plurality of slice gradient pulses, each slice gradient pulse being applied in parallel with a corresponding one of the plurality of saturation pulses.

22. The system of claim 19, wherein the at least one slice gradient pulse consists of only a single slice gradient pulse applied in parallel with all the plurality of saturation pulses.

23. The system of claim 19, wherein the pre-sequence includes a plurality of gradient spoiler pulses each of which is applied to the subject after a corresponding one of the plurality of saturation pulses.

24. The system of claim 19, wherein the pre-sequence includes a gradient spoiler pulse applied to the subject for the first time after all the plurality of saturation pulses are applied.

25. The system of claim 19, wherein each of the plurality of saturation pulses causes a magnetic spin in the pre-saturated slice to turn at a flip angle of less than 100 degrees.

26. The system of claim 19, wherein at least one of the plurality of saturation pulses causes a magnetic spin in the pre-saturated slice to turn at a flip angle that is substantially different from remaining saturation pulses.

27. The system of claim 19, wherein the slice gradient defines the pre-saturated slice to be substantially in parallel with the imaging slice.

28. The imaging method of claim 20, wherein the pre-sequence includes at least one slice gradient pulse applied in parallel with the plurality of saturation pulses for determining a spatial position of the pre-saturated slice differently from a spatial position of the imaging slice.

29. The imaging method of claim 28, wherein the pre-sequence includes at least one gradient spoiler pulse applied to the subject for the first time after all the plurality of saturation pulses have been applied.

30. A method for selective MR imaging of flowing nuclei, said method comprising:

(a) performing at least one MR image data acquisition sequence for a selected volume to be imaged; and (b) just prior to each said at least one MR image data acquisition sequence applying a pre-sequence of plural MR saturation pulses to a selected spatially offset volume that is upstream or downstream from the volume to be imaged with respect to said flowing nuclei, said plurality of saturation pulses providing an MT effect.

* * * * *